Figure 1:
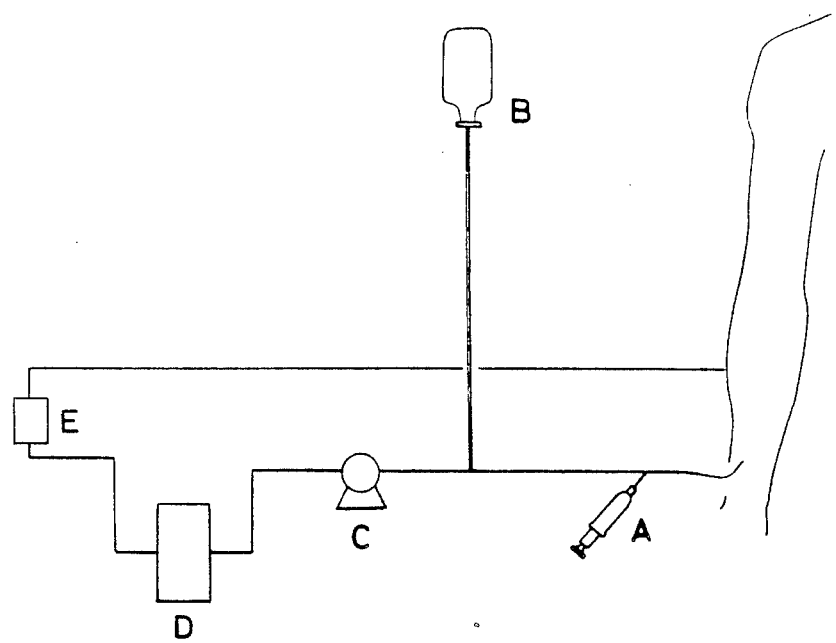

United States Patent [19]

Rossi

[11] Patent Number: 4,938,873

[45] Date of Patent: Jul. 3, 1990

[54] METHOD FOR PREVENTING BLOOD COAGULI FROM BEING FORMED IN THE EXTRA-BODY CIRCUIT OF DIALYSIS APPARATUS AND COMPOSITION USEFUL THEREFOR

[75] Inventor: Renato Rossi, Casnate-con-Bernate, Italy

[73] Assignee: Crinos Industria Farmacobiologica Spa, Villa Guardia Como, Italy

[21] Appl. No.: 261,539

[22] Filed: Oct. 24, 1988

[30] Foreign Application Priority Data

Oct. 23, 1987 [IT] Italy ................................ 22399 A/87

[51] Int. Cl.$^5$ .............................................. B01D 61/24
[52] U.S. Cl. .................................... 210/646; 210/647; 604/5
[58] Field of Search ................ 210/644, 645, 646, 647; 604/4, 5, 6

[56] References Cited

U.S. PATENT DOCUMENTS

| | | | |
|---|---|---|---|
| 3,770,720 | 11/1973 | Butti et al. | 536/24 |
| 3,829,567 | 8/1974 | Butti et al. | 536/24 |
| 3,865,726 | 2/1975 | Chibata et al. | 210/258 |
| 3,899,481 | 8/1975 | Butti et al. | 536/29 |
| 3,946,731 | 3/1976 | Lichtenstein | 210/647 |
| 4,649,134 | 3/1987 | Bonomini | 514/44 |
| 4,693,995 | 9/1987 | Prino et al. | 514/44 |

OTHER PUBLICATIONS

C. Mion et Alii: "Haemodialysis without Herparin, a Possible Benefit from Use of Ticlopidine in End Stage Renal Disease Haemodialysis Patients", Thromb. and Haemostas. 46 262, 1981.
S. M. Rajah et Alii: "Evaution of Five Antiplatelet Regimens in Haemodialysis: Prevention of Platelet Deposition and Thrombus Formation", Thromb and Haemostas. 50 61, 1983.
Chronique OMS liste 21 (Suppl. to n. 5 vol. 35 1981).
S. Cocheri et alii: "Effect of Fibrinolysis on a New Antithrombotic Agent: Franction P (Defibrotide). A Multicenter Trial", Int. J. Clin. Pharm. Res. II (3) 227-245, 1982.
G. Prino et Alii: "Indagini Preliminari Sull'attivita Fibrinolitica, Nell'Animale e Nell'Uomo, Di Una Nnuova Sostanza Presente in Diversi Organi Amimali", Simposio Internazional, "La Ricerca Sciefifica in Italia", Roma, Oct. 1975, pp. 557-560 (Proceedings).
R. Niada et Alii: "Antithrombotic Activity of Polydeoxyrbonucleotides of Mammalian Origin (Laboratory Code: Franction P) in Experimental Animals", Thromb. and Haemostas. 42 388, 1979.
G. Prino et Alii: "Antithrobotic Acitivity of a Polydesoxynucleotidic-Like Substance", Extract from volume (A. Strando ed.), Advances in Coagulation, Ibinolysis, Platelet Aggregation and Therosclerosis, European Symposium of S. Flavia Palermo, Oct. 1976), proceedings pp. 282-289.
E. Mozzi et Alii: "Effectiveness of Defibrotide for Prophylaxis of Deep Venous Thrombosis After General Surgery: a Double Lind Placebo-Controlled Clinical Trial", Haemostasis 16, Suppl. 1, pp. 36-38, 1986.
N. Ciavarella et Alii: "Effectiveness of Defibrotide for Prophylaxis of Deep Venous Thrombosis in Gynecological Surgery: a Double-Blind, Placebo-Controlled Clinical Trial", Haemostasis 16, Suppl. 1, pp. 39-41, 1986.
A. Rizz et Alii: "Profilassi Con Defibrotide Delle Bosi Venose Profonde in Chirurgia Toracica", Minerva Medica 78, 745-750, 1987.
R. Niada et Alii: "Antithrobotic Activity of a Polydeoxyribonucleotidic Substance Extracted from Mam- (List continued on next page.)

Primary Examiner—W. Gary Jones
Attorney, Agent, or Firm—Armstrong, Nikaido, Marmelstein, Kubovcik & Murray

[57] ABSTRACT

The introduction of Defibrotide, as a bolus or by infusion, upstream of the dialysis membrane of the extra body circuit of apparatus for the extra-body dialysis prevents coaguli from being formed in the blood stream.

8 Claims, 1 Drawing Sheet

OTHER PUBLICATIONS malian Organs: a Possible Link with Prostacyclin", Thromb. Res. 23, 233–246, 1981.

J. R. O'Brien et Alii: "The Effect in Humans of Defibrotide I.V. on Mumerous Blood Parameters", Haemostasis, vol. 14, 123, 1984.

L. Mussoni et Alii: "Activation of Plasma and Vasular Fibrinolytic Activity by a Polydeoxyribonucleotidic Substance, Fraction P, in Rats and Rabbits", VII Int. Cong. Thromb. Haem., Thromb. and Haemostas. 42 388, 1979.

A. Kumar et Alii: "Endothlial Function Modulation and Control of Vascular and Thrombotic Disorders: Experimental Results with a Polydeoxyribonucleotide Agent Defibrotide", The American Society of Hematology, 28th Annual Meeting, Dec. 6–9, 1986–San Francisco–Calif., Blood 68 n.5 Suppl. 1, Abstract n. 1302.

A. M. Pogliani et Alii: "Studio di Bioequivalenza di Due Schemi Posologici di Defibrotide su Parametri Della Fibrinolisi in Soggetti Volotari Sani", Farmaci e Terapia, vol. IV, No. 2, 94–98, 1987.

G. Czimeci et Alii: "Corrective Effect of Defibrotide on Altered Endotlium Cell Function in Atherosclerosis", Thromb. and Haemostas. 54 87 1 85.

METHOD FOR PREVENTING BLOOD COAGULI FROM BEING FORMED IN THE EXTRA-BODY CIRCUIT OF DIALYSIS APPARATUS AND COMPOSITION USEFUL THEREFOR

The present invention relates to the hemodialysis or extra-body dialysis and more specifically to a method for preventing blood coaguli from being formed in the extra-body circuit of hemodialysis apparatus.

It is also an object of the present invention the use of a specific active substance, in form of a composition, for such a preventing action.

The hemodialysis or extra-body dialysis is a therapeutical instrument, very widespread in the hospital practice, and ensures the daily survival of thousand of persons suffering from chronical kidney insufficiency. The haemodialysis, moreover, is applied also in the treatment of patients who, either accidently or willingly, have taken poisons or an excessive amount of drugs.

This technique is essentially based on the transfer of the solutes dissolved in the blood, through a semipermeable membrane, to the washing liquid or dialysis liquid which flows onto the other side of the membrane in countercurrent direction with respect to the blood flow.

These solutes are obviously substances which are toxic or the presence of which in the blood is anyhow undesired or excessive.

Said transfer takes place with a rate which is proportional to the concentration gradients existing for the said solutes between the two liquids; consequently the product of the cells catabolisms shall migrate through the membrane into the washing solution and viceversa the substances dissolved in the aforesaid liquid, such as per example glucose or several electrolites, shall pass into the blood.

An apparatus for the carrying out of the extra-body dialysis is schematically shown in FIG. 1.

The blood is taken from the vein or from the arteriovenous shunt of the patients and by means of a pump C is conveyed to a dialyser D and then passed through a filter E having also the function of trapping and retaining air or gas bubbles.

The blood, upon being dialysed and filtered, returns then to the body circuit. During the dialysis it is important to avoid the coagulation of the blood in the extra-body circuit, firstly since the patient blood would been in this manner become poor of erythrocytes. Secondly, the pores of the membrane would be progressively obstructed by these coaguli and the prosecution of the operation would become impossible.

In order to avoid this drawback, to date, the blood in the extra-body circuit has been added with a substance suitable to prevent to coagulation thereof.

The substance which is more commonly used in this connection is the heparin at dosages of between 5,000 and 10,000 units. Heparin is administered according to two different and equally effective routes:

(a) an initial injection carried out simultaneously with the beginning of the dialysis, in a point of the pipe conveying the blood from the patient to the dialyser (point A in FIG. 1), using an amount of heparin corresponding to half of that to be globally administered.

This first administration is followed by other two administrations, with intervals of 1.30 hours, with heparin doses corresponding each one to one fourth of the total one.

(b) Continuously, by diluting heparin in a suitable volume of physiological solution, generally 250 ml, and connecting the related bottle B (FIG. 1) to the afore mentioned conveying pipe.

However this substance has different parameters and distribution areas in the human body, whereby it is possible that, coming back in the circulation through the lymph, the heparin has an anti-coagulating effect for the patients for some hours after the dialysis.

For this reason in the patients undergoing dialysis under the above indicated conditions, both for some time after the dialysis and at determined times the coagulation time is assessed.

Depending on the values of this parameter consequent doses are then administered of an antidote of heparin, namely protamine.

Moreover in the patient in which a contraindication exists as regards the prolungation of the coagulation time (for example owing to recent traumas, surgical events, scaldes and an anamnesis which can be referred to bleeding ulcers) the use of the above described technique has evidently relevant risks.

Under these circumstances, alternatively, the peritoneal dialysis can be used which although being versatile and under some points of view less complex than the above technique, has equally some use limits. For example, it can not be used in patients which have undergone recent surgical intervention to the abdomen.

Summing up, even if already used by several years, the use of heparin in the haemodialysis, as already stated, is affected by several drawbacks.

Lastly it must not be forgotten that this anti-coagulant may also induce in the dialyzed patients a slight form of anemy as caused by hematic losses at the level of the digesting tract.

In order to solve these problems, the use of ticlopidine, a platelet anti aggregating drug, has been recently proposed as a partial or total substitute for heparin.

This drug is administered by oral route at doses of between 250 and 500 mg/kg. The results obtained to date are not conclusive: from one side, as a matter of fact, the possibility has been put into evidence of fully substituting heparin with ticlopidine (Mion C. et Alii "Haemodialysis without heparin, a possible benefit from the use of ticlopidine in end stage renal disease hemodialysis patients" Thrombos. and Haemostas. 46, 262, 1981), whereas from the other side it has been observed that under like experimental conditions the drug was not able to prevent the deposition of blood coaguli onto the membrane of the dialyser (Rajah S.M.et Alii "Evaluation of five antiplatelet regimens in haemodialysis: prevention of platelet deposition and thrombus formation" Thrombos. and Haemostas. 50, 61, 1983).

It is furthermore known that the regular administration of ticlopidine induces possible side effects of hematologic type, such as for example the prolungation of the bleeding time.

As a conclusion, even with this drug is seems not to be possible to solve in an effective and definite manner the aforesaid limitations of hemodialysis which occur by employing heparin.

From the above panorama the requirement is clearly seen of being able of carrying out the hemodialysis without the simultaneous and undesirable consequence of changing in any manner the patients hemostasis.

It has been now found and is main object of the present invention that the above identified problem is substantially solved by using the Defibrotide (D.C.I. Chronique O.M.S. 35 5 suppl. 4, 1981) which is chemically defined as a polydeoxyribonucleotide obtained by extraction from animal organs (U.S. Pat. Nos. 3,770,720 and 3,899,481, as well as European Patent Application No. 87.902.502.1.

The pharmacological and clinical properties of Defibrotide are known and are the subject of patents and of a number of scientific publications.

As a matter of fact it is known that this substance is endowed with a relevant profibrinolitic activity (U.S. Pat. No. 3,829,567 and S. Coccheri et Alii: "Effect on fibrinolysis of a new antithrombotic agent: Fraction P. (Defibrotide)" Int. J. Clin. Pharm. Res. II (3) 227-245 1982) whereas it has no influence on the hemocoagulating parameters (S. Coccheri, Supra; G. Prino et Alii: "Indagini preliminari sull'attività fibrinolitica, nell-'animale e nell'uomo, di una nuova sostanza presente in diversi organi animali" Simposio Internazionale "La ricerca scientifica nell'industria farmaceutica in Italia" Roma, ottobre 1975, Ferro Edizioni, Milano, 1977, pp 555-560).

The antithrombotic activity of the drug has been the subject of a number of studies (R. Niada et Alii: "Antithrombotic activity of polydeoxyribonucleotidic substances of mammalian origin (laboratory Code Fraction P) in experimental animals". VII International Congress on thrombosis and haemostasis, London - Jul. 1979, Thrombos. Haemostas. 42 388 1975; G. Prino at Alii "Antithrombotic activity of a polydeoyribonucleotidic-like substances (fraction P)" in A. Strano "Advances in coagulation, fibrinolysis, platelet aggregation and atherosclerosis" European Symposium of S. Flavia (Palermo, Oct. 1976) Proceedings page 282-89 CEPI Roma 1978; E. Mozzi et Alii "Effectiveness of Defibrotide for prophylaxis of deep venous thrombosis after general surgery: a double blind, placebo-controlled clinical trial" VIII International Congress on Thrombosis (Istanbul, Jun. 1984) Defibrotide Symposium Proceedings, Haemostasis 1986, 16 S1-36-38; Ciavarella N. et Alii: "Effectiveness of Defibrotide for prophylaxis of deep venous thrombosis in gynecological surgery: a double blind placebo-controlled clinical trial" VIII International Congress on Thrombosis, Haemostasi 1986, 16 S1 39-41; A. Rizzi et Alii: "Profilassi con Defibrotide delle trombosi venosi profonde in chirurgia toracica" Minerva Medica 78, 11 745-750 1987).

Defibrotide however has no platelet anti aggregating type effect (R. Niada et Alii: "Antibrombotic activity of a polydeoxyribonucleotidic substance extracted from animal organs; a possible link with prostacyclin" Thromb. Res. 23, 233-246, 1981; J.R. O'Brien et Alii: "The effects in humans of Defibrotide i.v. on numerous blood parameters" 7th International Congress on Fibrinolysis (Venice Mar. 1984) Abstract n. 227, Haemostasis 14, 121, 1984).

The antithrombotic properties thereof as above mentioned have been explained by demonstrating that the drug induces an increase in the circulation of the tissue activator of plasminogen (L. Mussoni et Alii: "Activation of plasma and vascular fibronolytic activity by a polydeoxyribonucleotidic substance, Fraction P, in rats and rabbits" "VIIth Interational Congress on Thrombosis and Haemostasis (London, Jul. 1979) Abstract 0922. Thrombos. Haemostas. 1979, 42, 388; A. Kumar et Alii; Endothelial function modulation and control of vascular and thrombotic disorders: experimental results with a polydeoxyribonucleotide agent Defibrotide". The American society of Hematology, 28th Annual Meeting, Dec. 6-9 1986, San Francisco-Calif., Blood 68 (5) 365A Abstract n. 1302 1986; E.M. Pogliani et Alii: "Studi di bioequivalenza di due schemi posologici su parametri della fibrinolisi in soggetti volontari sani" Farmaci e Terapia IV 2 1 1987) and of prostacyclin (Niada R. et Alii: "Antithrombotic activity of a polydeoxyribonucleotidic substance extracted from ammalian organs" see above; G. Cizmeci: "Corrective effect of Defibrotide on altered endothelium cell function in atherosclerosis" Xth International Congress on Thrombosis and Haemostasis, Jul. 14, 1985, Thrombos. Haemostas. 54(1) 1 372 1985).

From the above cited literature it is evident that the lack of platelet anti-aggregating activity and of influence on the hemocoagulating parameters shown by the Defibrotide together with its demonstrated antithrombotic and profibrinolytic efficacy might possibly only suggest the use of the Defibrotide it self as regards the elimination already formed of blood coaguli already formed.

As it will appear, on the contrary, from the following considerations and from the experimental tests already carried out, the feature which is mostly surprising of the present invention is that the introduction of Defibrotide at the beginning of the dialysis treatment, namely simultaneously with the beginning of the flow of the blood taken from the patient into the extra-body circuit, which introduction is carried out upstream of the dialyzer and of the filter (FIG. 1), preferably upstream of the circulation pump, has shown to be fully effective in preventing coagulation phenomena of the blood in the extra-body circuit, avoiding at the same time the said drawbacks found with heparin and the other drugs, namely mainly the action on the hemocoagulating parameters. Moreover a peculiar feature of the use of the drug in this therapeutical system is that the activity of Defibrotide in preventing coagulation phenomena in the extra-body circuit occurs, differently from heparin, at different doses depending on the administration route which is used. More particularly, it has been found and is another object of the present invention that the efficacy of Defibrotide in this therapeutical application is evident at lower doses for the "in bolus" administration (process "A" as above described for heparin) with respect to the continuous infusion (process "B").

Coming back to the object of the present invention, Defibrotide has been initially used in a group of 9 patients undergoing dialytic treatments with a frequency of three times of per week. The drug was administered according to the process "A" as above described with respect to heparin.

More precisely, at the beginning of the dialysis 2.5 ml of solution containing 200 mg of substance were injected; the same dose was repeated after 1.5-2 hours.

At the end of the first week of the treatment, for a total of 9 dialysis treatments per patient, owing to the fact that no drawbacks of any type were found as regards the blood circulation in the apparatus, the experimental testing has been broadened to a greater number of patients.

There have been thus treated 54 patients. It has been found that in some circumstances, was necessary it, after 3-4 hours from the beginning, a third administration carried out with the same conditions of the previous ones.

1860 dialysis treatments have been globally carried out, corresponding to more than two months of treatment for each patient.

In all these experiments Defibrotide confirmed, without exception, to be able to prevent the coagulation of blood in the extra-body circuit and the tolerability has been the optimum one in all the treated patients.

No significant variation have been moreover observed as regards the following hemocoagulating parameters, as determined before and after the dialysis: prothrombine time, partial thromboplastine time, fibrinogen, anti-thrombine III and coagulum retraction.

The active substance has been also the object of preliminary tests to assess if it was possible, as for the heparin, the administration according to the proceeding according to the method "B" as before described. To this end 400 mg of substance have been diluted to the volume of 250 ml and then continuously infused. Under these conditions, however, it was observed that Defibrotide was not able to fully prevent the forming of coaguli.

As a caution it was then necessary to administrate heparin doses globally comprised between 1200 and 2500 units.

It has been found that on the contrary such an addition is not necessary for Defibrotide doses greater than 500 mg, preferably between 600 and 800 mg.

From the above reported experimental work it is clear that the present invention resides both in the method for the prevention of the forming of blood coaguli in the extra-body circuit of dialysis apparatus, and in the use of Defibrotide in such a method.

More specifically:

(a) the method of the present invention is characterized in that at least at the beginning of the dialysis treatment in the extra-body circuit upstream of the dialysis membrane an effective amount of Defibrotide is introduced, simultaneously with the inlet of the blood in the extra-body circuit, said initial introduction being possibly followed by the introduction of a further amount of Defibrotide.

(b) According to a first embodiment of the present invention the initial introduction of Defibrotide is carried out as a bolus, namely as only one injection, preferably upstream of the circulation pump of the extra-body. According to this embodiment the initial introduction of Defibrotide contemplates a dosage of about 200 mg, the same dose being injected 1.5–2 hours after the beginning of the dialysis treatment.

(c) According to a second embodiment of the present invention the introduction of Defibrotide takes place by continuous infusion of a dose of at least 500 mg, said infusion beginning simultaneously with the introduction of the blood taken from the patient into to the extra-body circuit. The preferred dosage of Defibrotide in this second embodiment is 600–800 mg.

(d) According to a variation of this second embodiment of the method of the invention the dosage of Defibrotide is maintained at lower levels, of the same order as that of the method of bolus introduction, with the cautional addition of heparin in doses reduced by 75% or more with respect to the doses normally used in the dialysis treatment according to the prior art, obviously reducing in a remarkable manner the known drawbacks related to the use of heparin.

(e) The use of Defibrotide according to the present invention contemplates the use of compositions which can be administered by injection or infusion as those reported in the following examples I and II.

Without putting undue limitations to the present invention, it seems worth to mention that, also on the basis of the action mechanism already known and demonstrated for the Defibrotide, namely the development induced in the vessel endothelium of a tissue activator of the plasminogen and of prostacyclin, it was absolutely unforeseable that Defibrotide in a fully different situation, as it is obviously that which occurs in the extra-body circuit, would be able to give place to the observed phenomenon which is the object of the present invention.

This novel and surprising property of Defibrotide is particularly evident at the beginning of the dialysis, when the blood to which the Defibrotide solution has been added fills the apparatus.

In this situation, as a matter of fact, the substance at the above referred doses, is able to prevent the blood coagulation under conditions in which the above mentioned action mechanism can not evidently apply.

The forms which can be used in this new application of Defibrotide can be realized as vials and lyophilized compositions, some examples of which are hereinafter reported.

EXAMPLE I

| Vial Composition | | |
|---|---|---|
| Defibrotide | 200 mg | 400 mg |
| Bihydrated trisodium citrate | 25 mg | 50 mg |
| Bidistilled H$_2$O enough to | 2.5 ml | 4 ml |

EXAMPLE II

| Lyophilized Composition | |
|---|---|
| Defibrotide | 1 g |
| Sorbitol | 500 mg |
| to be diluted, at the time of the use, to 10–15 ml with distilled water. | |

The above description is specifically referred to Defibrotide; however it is foreseable that other substances of natural origin having fibrinolytic activity and essentially devoid of anticoagulating activity may find like use and in this sense are contemplated by the present invention.

I claim:

1. A method for preventing the formation of blood coaguli in an extracorporeal hemodialysis apparatus, said apparatus comprising a first means for transporting blood from a patient to a dialyzer, a hemodialysis membrane for dialyzing the blood transported thereto, and a second means for returning the dialyzed blood to the patient, which comprises introducing defibrotide into the blood in said first means upstream of the dialyzer in an amount effective to prevent the formation of blood coaguli in said apparatus.

2. A method according to claim 1, wherein the amount of defibrotide introduced is at least 200 mg.

3. A method according to claim 1, wherein the defibrotide is administered in a single dose.

4. A method according to claim 1, wherein the defibrotide is introduced at intervals.

5. A method according to claim 1, wherein the defibrotide is introduced by continuous infusion.

6. A method according to claim 5, wherein the amount of defibrotide introduced is at least 500 mg.

7. A method according to claim 6, wherein the amount of the defibrotide introduced is 600–800 mg.

8. A method according to claim 1, wherein the hemodialysis apparatus includes a pump for circulating blood through said apparatus and the defibrotide is introduced upstream of the pump.

* * * * *